US00PP15637P2

(12) United States Plant Patent
Vandenberg

(10) Patent No.: US PP15,637 P2
(45) Date of Patent: Mar. 8, 2005

(54) CARNATION PLANT NAMED 'YODER MIST'

(50) Latin Name: *Dianthus caryophyllus*
Varietal Denomination: Yoder Mist

(75) Inventor: Cornelis P. Vandenberg, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 47 days.

(21) Appl. No.: 10/818,355

(22) Filed: Apr. 5, 2004

(51) Int. Cl.[7] ..... A01H 5/00
(52) U.S. Cl. ..... Plt./274
(58) Field of Search ..... Plt./274

*Primary Examiner*—Kent Bell
(74) *Attorney, Agent, or Firm*—C. A. Whealy

(57) ABSTRACT

A distinct cultivar of Carnation plant named 'Yoder Mist', characterized by its pure white-colored flowers; early and freely flowering habit with about nine to ten flower per flowering stem; fragrant flowers; good postproduction longevity with flowers maintaining good substance and color for about ten days in an interior environment after shipping; and resistance to *Fusarium oxysporum*.

2 Drawing Sheets

Botanical classification: *Dianthus caryophyllus* cultivar Yoder Mist.

BACKGROUND OF THE INVENTION

The present invention relates to a new and distinct cultivar of Carnation plant, botanically known as *Dianthus caryophyllus* and hereinafter referred to by the name 'Yoder Mist'.

The new Carnation is a product of a planned breeding program conducted by the Inventor in Salinas, Calif. and Suba, Cundinamarca, Colombia, South America. The objective of the breeding program is to create new cut Carnation cultivars having long flowering stems, early flowering, attractive flower color, and good flower form and substance.

The new Carnation originated from a cross-pollination made by the Inventor in 1996, in Salinas, Calif., of a proprietary selection of Carnation identified as code number 0014, not patented, as the female, or seed, parent, with a proprietary selection of Carnation identified as code number 1396, not patented, as the male, or pollen, parent.

The cultivar Yoder Mist was discovered and selected by the Inventor as a flowering plant within the progeny of the stated cross-pollination in a controlled environment in Suba, Cundinamarca, Colombia, South America in June, 1997. The selection of this plant was based on its flower color and good flower form and substance.

Asexual reproduction of the new Carnation by terminal cuttings in Suba, Cundinamarca, Colombia, South America since July, 1997, has shown that the unique features of this new Carnation are stable and reproduced true to type in successive generations.

SUMMARY OF THE INVENTION

The cultivar Yoder Mist has not been observed under all possible environmental conditions. The phenotype may vary somewhat with variations in environment such as temperature and light intensity without, however, any variance in genotype.

The following traits have been repeatedly observed and are determined to be the unique characteristics of 'Yoder Mist'. These characteristics in combination distinguish 'Yoder Mist' as a new and distinct cultivar of Carnation:

1. Pure white-colored flowers.
2. Early and freely flowering habit with about nine to ten flowers per flowering stem.
3. Fragrant flowers.
4. Good postproduction longevity with flowers maintaining good substance and color for about ten days in an interior environment after shipping.
5. Resistance to *Fusarium oxysporum*.

Plants of the new Carnation can be compared to plants of the parent selections. In side-by-side comparisons conducted in Suba, Cundinamarca, Colombia, South America, plants of the new Carnation and the parent selections differed in the following characteristics:

1. Plants of the new Carnation flowered earlier than plants of the parent selections.
2. Petals and petaloids of plants of the new Carnation were not as serrated as petals and petaloids of plants of the parent selections.

Plants of the new Carnation can be compared to plants of the cultivar Cantare, disclosed in U.S. Plant Pat. No. 12,191. In side-by-side comparisons conducted in Suba, Cundinamarca, Colombia, South America plants of the new Carnation and the cultivar Cantare differed in the following characteristics:

1. Plants of the new Carnation had better flower uniformity than plants of the cultivar Cantare.
2. Petals and petaloids of plants of the new Carnation were not as serrated as petals and petaloids of plants of the cultivar Cantare.
3. Plants of the new Carnation flowered about one week earlier than plants of the cultivar Cantare.

BRIEF DESCRIPTION OF THE PHOTOGRAPHS

The accompanying colored photographs illustrate the overall appearance of the new Carnation, showing the colors as true as it is reasonably possible to obtain in colored reproductions of this type. Colors in the photographs may differ slightly from the color values cited in the detailed botanical description, which accurately describe the colors of the new Carnation.

The photograph on the first sheet comprises a side perspective view of a typical flowering stem of 'Yoder Mist' grown as a spray-type cut Carnation.

The photograph on the second sheet comprises a close-up view of a typical flower of 'Yoder Mist'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Madrid, Cundinamarca, Colombia, South America under conditions which approximate commercial practice in a single-layer polyethylene-covered greenhouse. Four-week old rooted cuttings were planted in ground beds and pinched about three to four weeks later. During the production time, day temperatures ranged from 19 to 24° C.; night temperatures ranged from 4 to 12° C.; and light levels ranged from 3,000 to 5,000 foot-candles. Measurements and numerical values represent averages for six to ten typical flowering stems about 26 weeks after planting.

Botanical classification: *Dianthus caryophyllus* cultivar Yoder Mist.

Commercial classification: Miniature spray-type cut Carnation.

Parentage:

*Female, or seed, parent.*—Proprietary selection of *Dianthus caryophyllus* identified as code number 0014, not patented.

*Male, or pollen, parent.*—Proprietary selection of *Dianthus caryophyllus* identified as code number 1396, not patented.

Propagation:

*Type.*—Terminal tip cuttings.

*Time from sticking unrooted cuttings to planting.*—About four weeks.

*Root description.*—Fine, freely-branching.

Plant description:

*Flowering stem description.*—Aspect: Erect. Strength: Very strong, flexible. Length: About 84 cm. Diameter: About 4 mm. Internode length, between basal flower and next lowest internode: About 6.5 cm. Texture: Smooth. Color: Close to 144A, overlain with waxy bloom, close to 188A to 188B.

*Foliage description.*—Arrangement: Opposite; sessile. Aspect: Slightly concave; mostly upright, approximately 45° angle from vertical. Length: About 11.8 cm. Width: About 1.1 cm. Shape: Linear. Apex: Sharply acute to acuminate. Margin: Entire. Texture: Tough, leathery; waxy. Color: Developing foliage, upper and lower surfaces: Close to 147A, overlain with waxy bloom, close to 188A. Fully developed foliage, upper and lower surfaces: Close to 147B, overlain with waxy bloom, close to 188A.

Flowering description:

*Appearance.*—Single hemispherical flowers arranged in sprays. Freely flowering, with potentially one flower developing at every node; usually about nine to ten flowers developing per flowering stem.

*Flowering response.*—Year-round under greenhouse conditions; plants flower about 26 weeks after planting rooted cuttings.

*Postproduction longevity.*—Good postproduction longevity with flowers maintaining good substance and color for about ten days in an interior environment after shipping. Flowers persistent.

*Fragrance.*—Fragrant; spicy, clove-like.

*Flower size.*—Diameter: About 4.8 cm. Depth (height): About 4.3 cm.

*Flower buds* (*at stage of showing color*).—Length: About 2.7 cm. Diameter: About 1.3 cm. Shape: Oblong. Color: Towards the apex, close to 155B; towards the base, close to 146A.

*Petals/petaloids.*—Quantity per flower: About 32, imbricate. Length: About 4.2 cm. Width: About 2.3 cm. Shape: Roughly spatulate. Apex: Roughly rounded; finely serrated giving a fringed appearance, undulate. Lateral margins: Entire. Texture: Velvety, smooth, glabrous. Color: When opening, upper and lower surfaces: Close to 158D; iridescent. Fully opened, upper and lower surfaces: Close to 155D; iridescent.

*Sepals.*—Quantity: About 5 or 6, fused. Length: About 2.5 cm. Width: About 5 mm. Calyx diameter: Apex: About 8 mm. Base: About 6 mm. Shape: Roughly ovate. Apex: Acuminate. Texture: Tough, leathery; smooth; waxy, longitudinally ridged. Resistance to splitting: Very good, calyxes rarely split. Color: Upper surface: Close to 195C. Lower surface: Close to 146B.

*Reproductive organs.*—Androecium: Stamen number: About ten; most are transformed into petaloids. Stamen length: About 1.4 cm. Stamen color: Close to 155D. Anther size: About 2 mm by 1 mm. Anther shape: Oblong. Anther color: Close to 9D. Pollen: None observed. Gynoecium: Pistil quantity: Two. Pistil length: About 2.2 cm. Color: Close to 155D. Ovary size: About 6 mm by 5 mm. Ovary color: Close to 145B.

*Seed/fruit.*—Seed and fruit production have not been observed.

Disease/pest resistance: Plants of the new Carnation planted in soils heavily infested with *Fusarium oxysporum* have been observed to be highly resistant to *Fusarium oxysporum.* Plants of the new Carnation have not been observed to be resistant to other pathogens and pests common to Carnations.

It is claimed:

1. A new and distinct cultivar of Carnation plant named 'Yoder Mist', as illustrated and described.

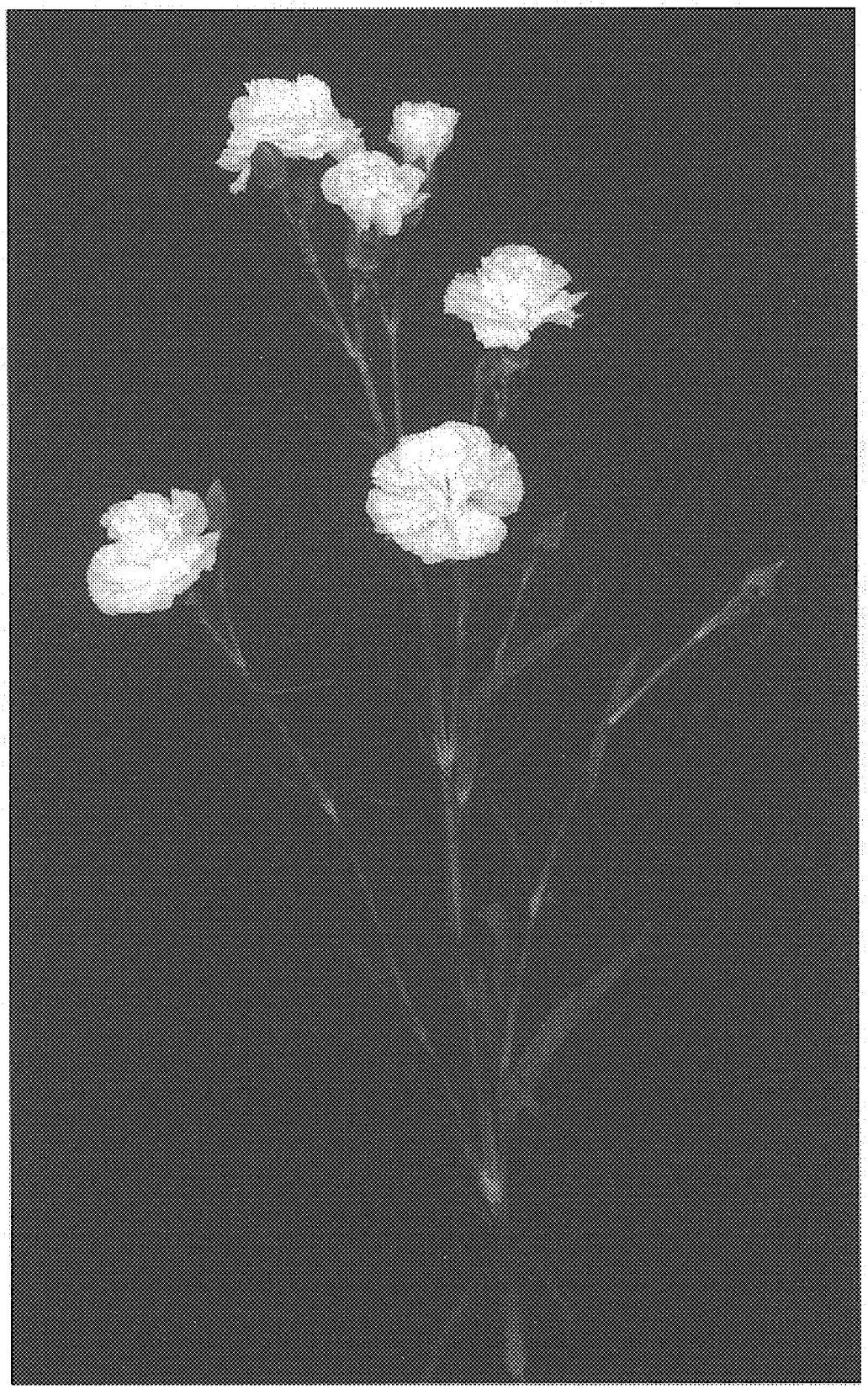

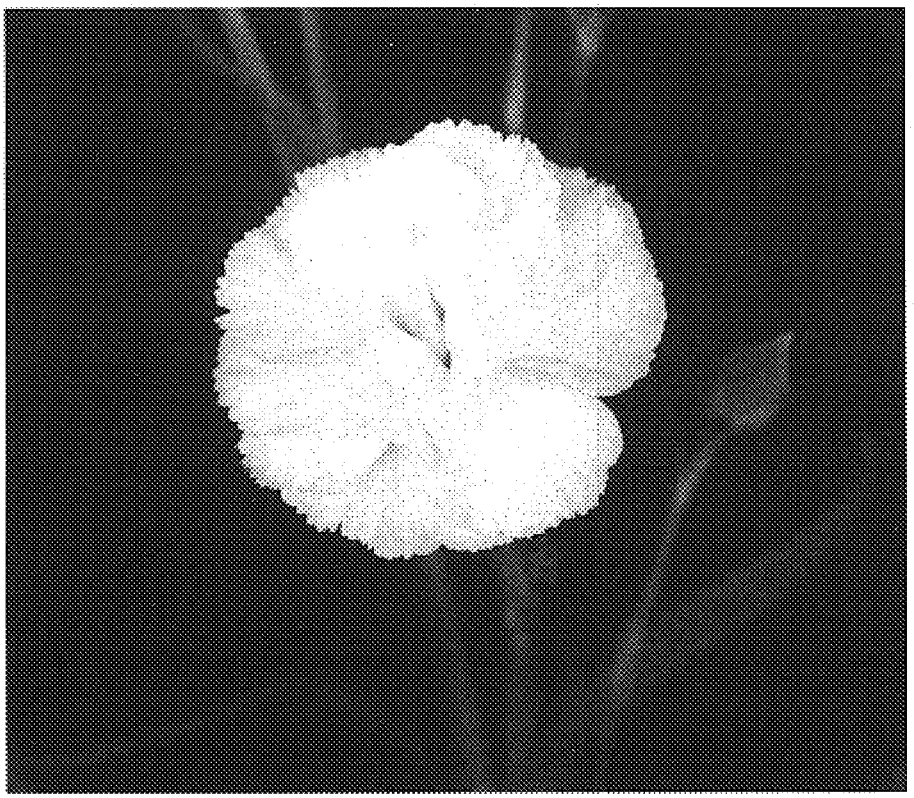

* * * * *